(12) United States Patent
Perez, III

(10) Patent No.: US 9,498,232 B2
(45) Date of Patent: Nov. 22, 2016

(54) ARTICULATING DRILL GUIDE

(71) Applicant: Arthrex, Inc., Naples, FL (US)

(72) Inventor: Arley Perez, III, Bonita Springs, FL (US)

(73) Assignee: Arthrex, Inc., Naples, FL (US)

( * ) Notice: Subject to any disclaimer, the term of this patent is extended or adjusted under 35 U.S.C. 154(b) by 357 days.

(21) Appl. No.: 14/044,289

(22) Filed: Oct. 2, 2013

(65) Prior Publication Data

US 2014/0114322 A1    Apr. 24, 2014

Related U.S. Application Data

(60) Provisional application No. 61/717,311, filed on Oct. 23, 2012.

(51) Int. Cl.
*A61B 17/17* (2006.01)
*A61B 17/16* (2006.01)

(52) U.S. Cl.
CPC ....... *A61B 17/1742* (2013.01); *A61B 17/1714* (2013.01); *A61B 17/1668* (2013.01)

(58) Field of Classification Search
CPC ..................................... A61B 17/17–17/1796
USPC ......................................................... 606/96
See application file for complete search history.

(56) References Cited

U.S. PATENT DOCUMENTS

| | | | | |
|---|---|---|---|---|
| 5,350,383 A * | 9/1994 | Schmieding | ....... | A61B 17/1764 606/103 |
| 5,562,664 A * | 10/1996 | Durlacher | .......... | A61B 17/1764 606/103 |
| 5,643,273 A * | 7/1997 | Clark | ................ | A61B 17/1764 606/102 |
| 5,968,050 A * | 10/1999 | Torrie | ................ | A61B 17/1714 606/102 |
| 7,442,195 B1 * | 10/2008 | Behrens | ............... | A61B 17/025 30/346 |
| 8,298,239 B2 * | 10/2012 | Re | ...................... | A61B 17/1714 606/87 |
| 8,323,289 B2 * | 12/2012 | Re | ...................... | A61B 17/1714 606/87 |
| 8,771,274 B2 * | 7/2014 | Homan | .............. | A61B 17/1764 606/80 |
| 2005/0273084 A1* | 12/2005 | Hinman | ................. | A61B 1/008 606/1 |
| 2006/0074383 A1* | 4/2006 | Boulais | ................ | A61B 1/0052 604/95.04 |
| 2007/0219550 A1* | 9/2007 | Thompson | ........... | A61B 1/0055 606/41 |
| 2009/0163766 A1* | 6/2009 | Torrie | .................. | A61B 17/025 600/102 |
| 2009/0281545 A1* | 11/2009 | Stubbs | ............... | A61B 17/1666 606/87 |
| 2010/0049196 A1* | 2/2010 | Re | ...................... | A61B 17/1764 606/88 |
| 2010/0049199 A1* | 2/2010 | Re | ...................... | A61B 17/1764 606/88 |

* cited by examiner

*Primary Examiner* — Zade Coley
(74) *Attorney, Agent, or Firm* — Rubin and Rudman LLP

(57) ABSTRACT

Drill guides and methods for maintaining contact on bone in areas where rigid instruments cannot access. The drill guide is an articulating drill guide that comprises an articulating mechanism for articulating and positioning the guide in at least two positions, i.e., an undeployed (non-articulated or straight) position and a deployed (articulated or bent) position. The articulating drill guide delivers guide wires, drills and/or additional instruments at any angle while maintaining contact to the bone.

8 Claims, 3 Drawing Sheets

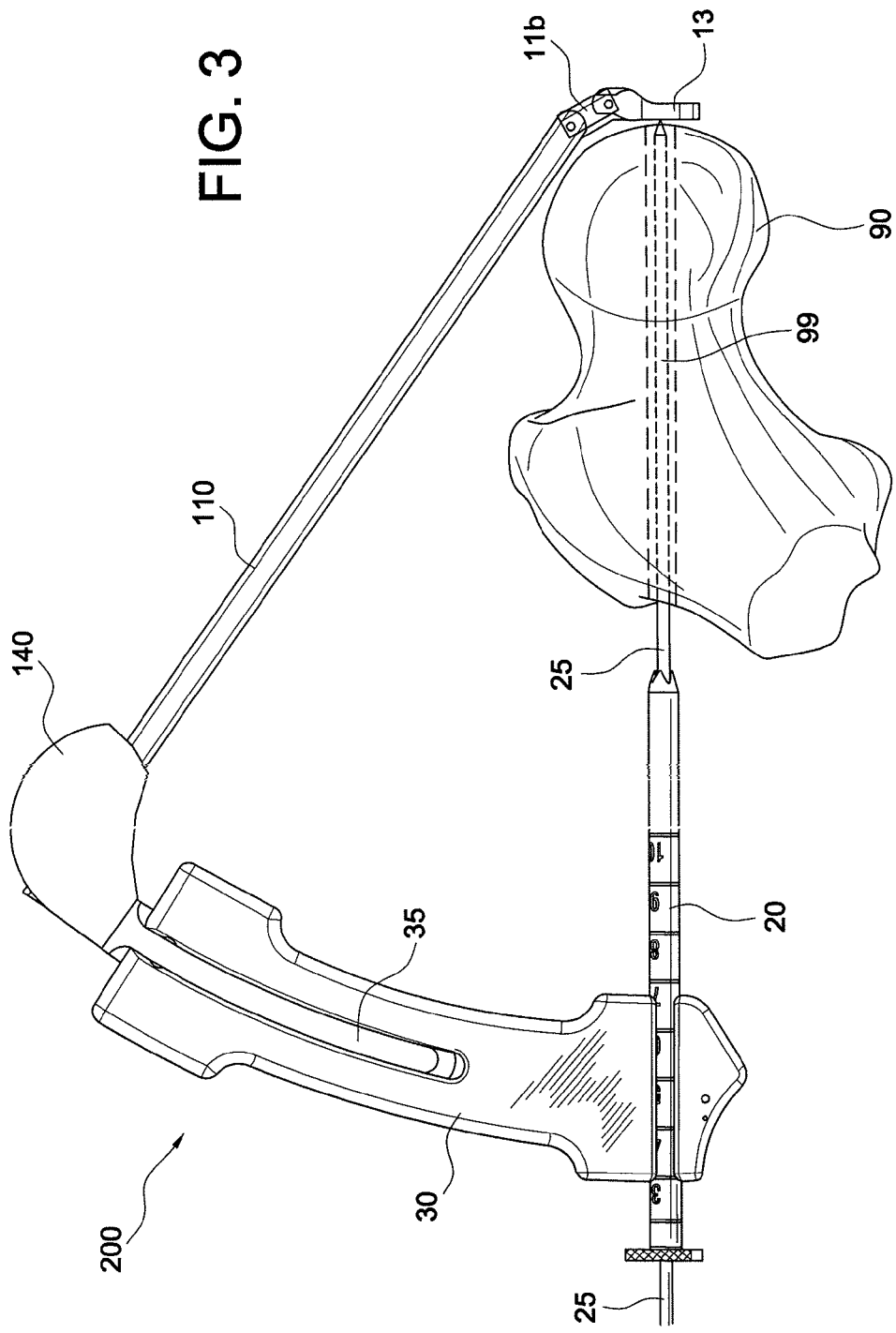

ARTICULATING DRILL GUIDE

CROSS-REFERENCE TO RELATED APPLICATIONS

This application claims the benefit of U.S. Provisional Application No. 61/717,311 filed Oct. 23, 2012, the disclosure of which is incorporated by reference in its entirety herein.

FIELD OF THE INVENTION

The present invention is directed to surgical instruments and, particularly, to a drill guide used in arthroscopic procedures.

BACKGROUND OF THE INVENTION

Arthroscopic procedures typically require a surgeon to work through a series of portals. For the hip joint, in particular, it is difficult to insert instrumentation through this series of portals. As a result, many RF devices designed for hip applications utilize a steerable mechanism which allows the device to enter the joint in a straight configuration/orientation and then curve, which effectively increases the surgeon's area of access within the joint.

There is a need for a femoral guide that confers the surgeon the ability to target any surface of the femoral head. Also needed is a guide that allows a surgeon the ability to specify a location on the femoral head from outside the joint. The drill guide should desirably maintain contact on the bone to protect the soft tissue surrounding the bone.

SUMMARY OF THE INVENTION

The present invention provides methods of surgery, systems and drill guides that maintain contact on the bone even in areas where rigid instruments cannot access the areas. Although the drill guides of the present invention have particular application to the hip joint, the drill guides may be employed in any ligament reconstruction, bone resurfacing and/or replacement in any kind of joint and are not limited to hip joint.

The drill guide of the present invention is an articulating drill guide that comprises an articulating mechanism for positioning the guide in at least two positions, i.e., an undeployed (non-articulated or straight) position and a deployed (articulated or bent) position. The articulating drill guide delivers guide wires, drills and/or additional instruments at any angle while maintaining contact to the bone.

An exemplary method of surgery with an articulating drill guide of the present invention comprises inter alia the steps of: (i) providing a drill guide including an articulating mechanism configured to articulate the drill guide in at least two positions, i.e., a first undeployed (non-articulated or straight) position and a second deployed (articulated or bent) position; (ii) inserting the articulating drill guide in a first (straight) position through a joint portal; (iii) articulating the drill guide from the first (straight) position to a second (articulated) position to target an area of the bone at the joint where rigid instruments cannot access; and (iv) conducting at least one surgical procedure relating to the target area of the bone.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 3 illustrates another exemplary articulating drill guide of the present invention (a hip articulating drill guide with an angular change) in the articulated position.

DETAILED DESCRIPTION OF THE PREFERRED EMBODIMENTS

Figure 1:
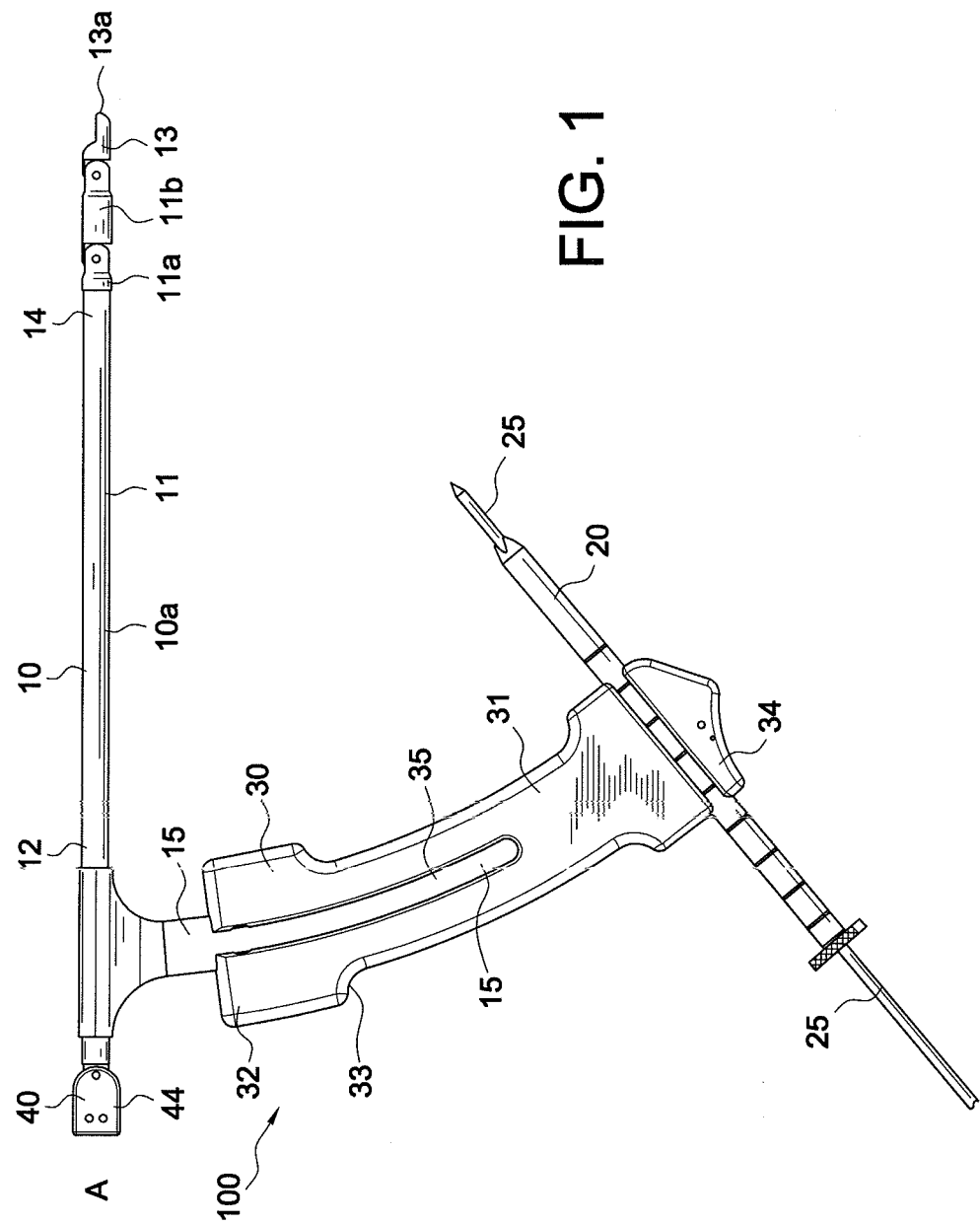
FIG. 1 illustrates an exemplary articulating drill guide of the present invention in the straight or non-articulated position.

The present invention provides methods of surgery, systems and articulating drill guides which maintain contact on the bone (even in areas where rigid instruments cannot access the areas) while placing drill guides and/or wires and/or additional instruments into the bone, at a specific target location or area of the bone. In a particular exemplary embodiment, the articulating drill guide of the present invention is used where femoral head targeting would be useful. Examples are femoral head resurfacing/replacement and ligament reconstructions (for example, teres ligament reconstruction) in hip or other reconstructions.

Although the drill guides of the present invention have particular application to the hip joint, the drill guides may be employed in any ligament reconstruction, bone resurfacing and/or replacement in any kind of joint and are not limited to hip joint.

The drill guide allows for minimally invasive bone targeting (for example, femoral head targeting). The drill guide may be employed in various surgical procedures, for example, torn ligament reconstruction and femoral head resurfacing/replacement, among others.

The drill guide of the present invention is an articulating drill guide that comprises an articulating mechanism for positioning the guide in at least two positions, i.e., an undeployed (non-articulated or straight) position and a deployed (articulated or bent) position. The articulating mechanism may include at least one cable (for example, a single cable or a plurality of cables) or may consist of a positioning arm mechanism designed to position the most distal end of an arm on a targeted bone surface area, as detailed below. In the embodiment where a plurality of cables are employed, and depending in which position the surgeon would like the articulating guide to be in, the surgeon would tension the particular cable designated for the particular position. The articulating mechanism may be also a device that is actuated with a drive unit and/or, alternatively, actuated manually, to position the articulated arm (the most distal end of the articulated arm) at the desired location on the bone. The articulating mechanism may optionally include a locking mechanism, so that the articulated arm can be locked and secured against accidental movement.

The articulating drill guide may be used with a guide handle or on its own. The articulating drill guide delivers guide wires, drills and/or additional instruments at any angle while maintaining contact to the bone.

An exemplary method of surgery with the articulating drill guide of the present invention comprises inter alia the steps of: (i) providing a drill guide including an articulating mechanism configured to articulate the drill guide in at least two positions, i.e., a first undeployed (non-articulated or straight) position and a second deployed (articulated or bent) position; (ii) inserting the articulating drill guide in a first (straight) position through a portal (for example, the hip portal); (iii) articulating the drill guide from the first (straight) position to a second (articulated) position to target an area of the bone (for example, the femoral head) where rigid instruments cannot access; and (iv) conducting at least one surgical procedure relating to the target area of the bone (for example, the femoral head).

Figure 2:
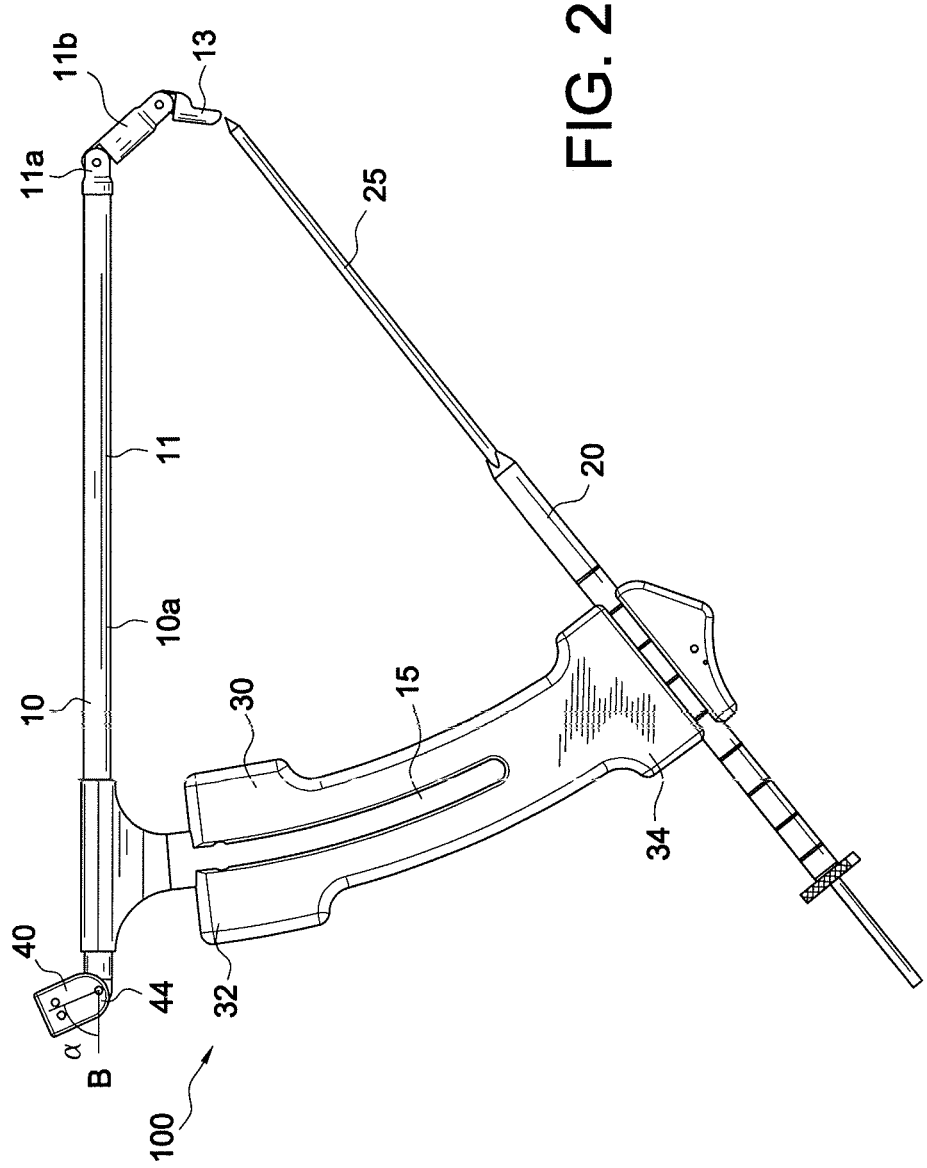
FIG. 2 illustrates the articulating drill guide of FIG. 1 in the bent or articulated position.

Referring now to the drawings, where like elements are designated by like reference numerals, FIGS. 1-3 illustrate articulating drill guides 100, 200 of the present invention which may be positioned on a bone (for example, the femoral head of the hip joint) at a specific location on the bone and following the normal curvature of the bone.

The articulating drill guide 100 includes a first guide member 10 and a second guide member 20 attached to a frame 30 (body 30) having a generally curved configuration. Frame 30 is defined by side surfaces 31, 33 which are narrow and have a generally arcuate shape. Frame 30 has a shape, thickness and configuration that allows it to comfortably fit in a surgeon/operator's hand. An arcuate slot 35 having a general rectangular cross-section is formed in the frame 30 extending about two thirds of the length of the frame 30. Arcuate slot 35 follows the shape of sides 31, 33 and is configured to receive a radial arm 15 to slide therein or to be securely affixed thereto (i.e., slidingly or non-slidingly connected thereto). The radial arm 15 has essentially the same arc as that of the arcuate slot 35 and sides 31, 33.

Frame 30 is also provided with first and second ends 32, 34 which allow attachments of the first and second guide members 10, 20, respectively, and as detailed below. The articulating drill guide 100 also includes an articulating mechanism 40 which is attached to the first guide member 10 (and in communication with it) to allow the first guide member 10 to articulate and to approximate the anatomical curvature of the bone, for example, of the femoral head of the hip joint, and as explained in more detail below.

The first guide member 10 may include a cylindrical shaft or tube 11 (which may be fully or partially cannulated) with a longitudinal axis 10a and provided with a proximal end 12 and a distal end 14. The first guide member 10 terminates in a plurality of articulating segments or members 11a, 11b, 13 which, when actuated, can articulate and bend as shown in FIG. 2 (showing only two segments 11b, 13 actuated/articulated/bent). The most distal segment 13 is preferably in the form of a hook or probe that terminates in an elongated rounded tip 13a. The surface of the hook or probe 13 is about concentrical to the targeted surface area of the bone. In this manner, when the first guide member 10 is actuated, at least one of the articulating segments articulates to allow hook or probe 13 to follow the contour of a bone surface that is being targeted.

The second guide member 20 is an exemplary drill sleeve that allows insertion of an instrument 25 (for example, a guide wire or a drill or any other surgical instrument) as shown in FIG. 2, once the target area of the bone has been identified (e.g., the area to be drilled/resurfaced) with probe 13.

Articulating mechanism 40 is attached to the first guide member 10 and in communication with it, to allow the first guide member 10 to articulate between at least two positions, i.e., a first, undeployed (non-articulated or straight) position and a second, deployed (articulated or bent) position. The articulating mechanism 40 may be any mechanism that allows articulation of last segments 11b, 13 to bend/move/articulate as shown in FIG. 2. For example, the articulating mechanism may be formed of a single deploying cable or wire 44 or, alternatively, may be formed of a plurality of deploying cables or wires 44 (for example, two deploying cables or wires). Regardless of the number of cables/wires, the articulating mechanism 40 allows for the articulation of the first guide member 10. Depending in which position the surgeon would like the articulating guide to be in, the surgeon would tension the particular cable(s) 44 designated for the particular position, for example, a different cable for each of articulating members 11b, 13. The articulating drill guide may be used with a guide handle or on its own.

FIG. 1 shows the drill guide 100 with the first guide member 10 in the first, undeployed (non-articulated or straight) position. FIG. 2 shows the drill guide 100 with the first guide member 10 in the second, deployed (articulated or bent) position. Pushing on actuating member 44 of the articulating mechanism 40 from position A (FIG. 1) to position B (FIG. 2) pivots the articulating tip 13 between the locations shown in FIGS. 1 and 2. In position A (FIG. 1), actuating member 44 of the articulating mechanism 40 extends about parallel to the longitudinal axis 10a of the cylindrical tube 11 (in axial alignment with it). In position B (FIG. 2), actuating member 44 of the articulating mechanism 40 extends non-parallel to the longitudinal axis 10a of the cylindrical tube 11 and forms an angle $\alpha$ with the longitudinal axis 10a.

Once the desired target area on the bone has been reached, the drill sleeve 20 may be tightened down with a locking device (for example, a twist knob or other similar device). Drill 25 (FIG. 2) is advanced through the drill sleeve 20, and into the bone, at a target area identified and delineated by articulating probe 13.

FIG. 3 illustrates another embodiment 200 of the present invention wherein articulating drill guide 200 shows an angular change for the drill guide (i.e., with an angular shift different from that of the articulating drill guide 100). The articulating drill guide 200 is about similar to guide 100 described above but differs in that the articulating drill guide 200 includes articulating mechanism 140 which is designed to allow positioning of first guide member 110 and of the segments 11b and 13, as shown in FIG. 3.

The articulating drill guide of the present invention may be used where femoral head targeting would be useful. Examples are femoral head resurfacing/replacement and ligament reconstructions.

An exemplary surgical method employing the articulating drill guide of the present invention comprises inter alia the steps of: (i) providing drill guide 100, 200 including an articulating mechanism 40, 140 configured to articulate the drill guide in at least two positions, i.e., a first undeployed (non-articulated or straight) position and a second deployed (articulated or bent) position; (ii) inserting the articulating drill guide 100, 200 in a first (straight) position through a joint portal; (iii) articulating the drill guide 100, 200 from the first (straight) position to a second (articulated) position to target an area of the bone where rigid instruments cannot access; and (iv) conducting at least one of bone resurfacing or replacement, or ligament reconstruction.

An exemplary method of hip joint surgery with the articulating drill guide of the present invention comprises inter alia the steps of: (i) providing drill guide 100, 200 including an articulating mechanism 40, 140 configured to articulate the drill guide in at least two positions, i.e., a first undeployed (non-articulated or straight) position and a second deployed (articulated or bent) position; (ii) inserting the articulating drill guide 100, 200 in a first (straight) position through a hip portal; (iii) articulating the drill guide 100, 200 from the first (straight) position to a second (articulated) position to target an area of the femoral head 90 where rigid instruments cannot access, so that a most distal end of the drill guide aligns with a center of the area of the femoral head where rigid instruments cannot access; (iv) aligning a second member 20 with the a most distal end of the drill guide; and (v) passing a surgical instrument through the second guide member 20 and through the femoral head 90 to conduct at least one of femoral head resurfacing or replacement procedure.

FIG. 3 illustrates articulating drill guide 200 positioned on femoral head 90 of a hip. Once the articulating drill guide 200 has been articulated to the second (articulated) position on the femoral head 90 (i.e., once the segment 11b and probe 13 have been articulated so that the probe 13 engages the target area of the femoral head where a rigid instrument cannot access), a drilling step is conducted to form at least one tunnel 99 (FIG. 3) through the bone 90 with exemplary drill 25. As shown in FIG. 3, the most distal end of drill 25 aligns with a center of the surface of the hook/probe 13 (which in turn is about concentric to the targeted surface area of bone 90).

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A drill guide comprising:
   a frame, a radial arm, a first guide member, a second guide member, and an articulating mechanism;
   wherein the frame has a generally curved configuration and comprises a first end with an arcuate slot configured to receive the radial arm and a second end configured to attach to the second guide member;
   wherein the first guide member is attached to the radial arm at an end of the radial arm opposite the end of the radial arm that is received by the frame and comprises a cylindrical shaft terminating in a plurality of articulating segments, wherein a most distal articulating segment is configured to articulate from a non-articulated position to an articulated position; and
   wherein the articulating mechanism is in communication with the first guide member and configured to articulate the most distal articulating segment of the first guide member from the non-articulated position to the articulated position.

2. The drill guide according to claim 1, wherein the arcuate slot extends about two thirds the length of the frame.

3. The drill guide according to claim 1, wherein the articulating mechanism is attached to the first guide member.

4. The drill guide according to claim 1, wherein the second guide member is a drill sleeve.

5. The drill guide according to claim 1, wherein the second guide member aligns with the most distal articulating segment of the first guide member when the most distal articulating segment in the articulated position.

6. The drill guide according to claim 3, wherein the articulating mechanism comprises at least one tensioning wire or cable.

7. The drill guide according to claim 6, wherein the at least one tensioning wire or cable actuates the most distal articulating segment from the non-articulated position to the articulated position.

8. The drill guide according to claim 1, wherein at least one of the articulating segments articulates to allow a probe to follow a contour of a bone surface.

* * * * *